(12) United States Patent
Tischendorf et al.

(10) Patent No.: US 7,759,948 B2
(45) Date of Patent: Jul. 20, 2010

(54) DISPOSABLE TOTAL DISSOLVED SOLIDS METER AND METHODS OF USE THEREOF

(75) Inventors: Andy Tischendorf, Campbellsport, WI (US); Santanu Roy, Faridabad (IN); Sanjeev Patel, Rourkela (IN); Roy Parker, Hawthorn Woods, IL (US); Manu Verma, New Delhi (IN); Dean Jarog, Villa Park, IL (US); Nanda K. Dash, Bhubaneswar (IN); Michael Lindfors, Whitefish Bay, WI (US)

(73) Assignee: Pentair Filtration Solutions, LLC, Brookfield, WI (US)

( * ) Notice: Subject to any disclaimer, the term of this patent is extended or adjusted under 35 U.S.C. 154(b) by 284 days.

(21) Appl. No.: 11/874,615

(22) Filed: Oct. 18, 2007

(65) Prior Publication Data

US 2009/0091338 A1    Apr. 9, 2009

Related U.S. Application Data

(60) Provisional application No. 60/977,967, filed on Oct. 5, 2007.

(51) Int. Cl.
*G01R 27/08* (2006.01)
*G01N 27/02* (2006.01)

(52) U.S. Cl. .................. 324/694; 210/746; 324/439

(58) Field of Classification Search ............... 324/694; 210/746
See application file for complete search history.

(56) References Cited

U.S. PATENT DOCUMENTS 3,774,105 A * 11/1973 Henning et al. .............. 324/449
3,990,066 A    11/1976 Malmgren
4,383,221 A    5/1983 Morey et al.
4,496,906 A *  1/1985 Clack ....................... 324/439

(Continued)

OTHER PUBLICATIONS

Hach—Conductivity Tester, Pocket Pal—Screenprint, obtained from www.hach.com/hc/search.product.details.invoker/PackagingCode=2686601/NewLin.

*Primary Examiner*—Timothy J Dole
*Assistant Examiner*—John Zhu
(74) *Attorney, Agent, or Firm*—Andrus, Sceales, Starke & Sawall, LLP

(57) ABSTRACT

A disposable meter for testing the level of total dissolved solids in a water source and a method of testing the concentration of total dissolved solids are herein disclosed. The disposable meter may include a body with at least water resistant properties, a first indicator, the energization of which is indicative of a threshold level measured total dissolved solids, a pair of electrodes wherein energization passing between the pair of electrodes completes a circuit, and circuitry disposed within the body connected to the first indicator and the pair of electrodes. The circuitry may be configured to commence energization to pass between the pair of electrodes, measure the conductivity of the water between the pair of electrodes, and energize the first indicator if the measured conductivity value exceeds a predetermined threshold value. The method of testing the concentration of total dissolved solids present in a water supply may include projecting a current between a first electrode and a second electrode, measuring the conductivity of the water between the electrodes, comparing the measured conductivity to a plurality of threshold values, and energizing an indicator in a matter that is correlated to the highest threshold value met by the measured conductivity.

12 Claims, 4 Drawing Sheets

U.S. PATENT DOCUMENTS

| | | |
|---|---|---|
| 4,762,611 A | 8/1988 | Schipper |
| 4,849,098 A | 7/1989 | Wilcock et al. |
| 4,851,818 A | 7/1989 | Brown et al. |
| 5,057,212 A | 10/1991 | Burrows |
| 5,126,041 A | 6/1992 | Weber et al. |
| 5,581,189 A | 12/1996 | Brenn |
| 6,058,718 A | 5/2000 | Forsberg et al. |
| 6,059,942 A * | 5/2000 | Barnes et al. ............... 204/269 |
| 6,073,580 A * | 6/2000 | Graupner et al. ......... 119/14.08 |
| 6,110,424 A * | 8/2000 | Maiden et al. ................ 422/24 |
| 6,217,744 B1 | 4/2001 | Crosby |
| 6,406,618 B1 | 6/2002 | O'Leary |
| 6,524,475 B1 | 2/2003 | Herrington et al. |
| 6,994,073 B2 * | 2/2006 | Tozzi et al. ................. 123/298 |
| 7,164,105 B2 * | 1/2007 | Godshalk et al. ............ 219/679 |
| 2002/0167322 A1* | 11/2002 | He et al. ..................... 324/441 |
| 2006/0144765 A1* | 7/2006 | Skwiot ....................... 210/85 |
| 2007/0205160 A1* | 9/2007 | Savage et al. ............... 210/746 |

* cited by examiner

DISPOSABLE TOTAL DISSOLVED SOLIDS METER AND METHODS OF USE THEREOF

CROSS REFERENCE TO RELATED APPLICATIONS

This application is claims priority of Provisional Application Ser. No. 60/977,967, filed on Oct. 5, 2007.

BACKGROUND

The term "dissolved solids" refers generally to any minerals, salts, metals, cations or anions that are dissolved in a water sample. Dissolved solids include many of the substances that impair water color, odor, taste, or overall water quality. Many industries, and the food service industry in particular, require that the water used be held to stringent standards such that the color, odor, or taste of the water does not have any adverse effect on the end product. Many available water supplies exceed the EPA's recommended maximum total dissolved solids (TDS) level of 500 parts per million (ppm); therefore treatment and monitoring of water sources for TDS levels is important to maintaining a desired water quality for particular industrial or commercial activities.

The monitoring of TDS levels from a water source can effectively help in determining the appropriate types of water processing and/or treatment that must be applied to the water to obtain a water output within a desired range of TDS levels.

Many types of water purification systems may be used to reduce the level of TDS from a water source. These water purification systems include distillation and deionization systems; however, the most thorough method of large-scale water purification is reverse osmosis filtering, wherein the water is forced under pressure through a semi-permeable membrane that allows water to pass through while removing most TDS contaminants.

The measurement of TDS in a water supply is not only important for determining the proper type of water purification system that should be used to treat used to treat the water, but is also important for the continual monitoring of the water from the purification system to ensure that the desired TDS output levels are being achieved. A detected rise in the measured TDS level may be indicative of increased contaminants in the water supply source, and a new or modified water purification system may be needed. Alternatively, the detected rise in measured TDS may be indicative of reduced filtering capacity, thus indicating that it is time to replace the filter. Specifically in monitoring the function of a reverse osmosis system, a rise in TDS levels may indicate a compromised membrane that may need replacement.

Devices and methods currently exist for monitoring the TDS in a water source. Many of these devices are based on the principle that the conductivity of the water being tested increases as the TDS in the water increases. Therefore, the TDS may be measured by inserting a pair of electrodes into the water to be tested and measuring the conductivity between the two electrodes experienced by a current passed between them. These TDS meters have been developed both as stationary in line systems that are inserted into the water purification system just prior to the water output, or may exist as portable, handheld device.

The handheld devices are popular for use by technicians in conducting field tests of water sources, either in preparation for recommending a new water purification system for a customer or as part of regular maintenance and water purification system check-up.

However, handheld TDS meters are not practical for casual use by a customer or a layman. This is due to the fact that handheld TDS meters are prohibitively expensive for consumers that may only use the handheld TDS meter once or twice a year, or for potential consumers interested in obtaining more information about their specific water filtering needs. In addition to the cost, some TDS meters are complex to operate and/or install such as to make it difficult for customers or layman to obtain accurate results. Additionally, many TDS meters display the measured TDS value in numeric form indicating the parts per million (ppm) of TDS. The lay consumer is not trained to interpret this measured value of TDS in ppms to understand TDS in ppms to understand the quality of the water source. The TDS meters that are available are intended for regular use and testing many water samples over time. Therefore it is not economically practical for a consumer to purchase one of the currently available TDS meters for annual or semi-annual water system testing. Furthermore, the expense of current handheld TDS meters makes it difficult for the wide spread dissemination in use of the TDS meters by all of the clients of a provider of water treatment products and services.

The TDS in a water supply may be alternatively monitored with the use of paper test strips that change color based upon the TDS level of the water in which they are placed. However, these test strips are typically difficult to properly use and interpret and do not identify the TDS level with a sufficient specificity in order to properly assess water purification needs, or to monitor the on-going function of an existing water purification system.

Therefore, it is desirable in the field of water purification services and monitoring for a disposable electronic TDS meter. Such a meter may be widely disseminated amongst current or potential water purification system and services customers for reliable monitoring of water supply TDS levels by customers that may not be trained in the specifics of water TDS monitoring.

BRIEF DISCLOSURE

As disclosed and illustrated by the embodiments herein a disposable total dissolve solids (TDS) meter may be used by a technician or a consumer at a remote location for testing the level of total dissolved solids in a water supply. The TDS meter may comprise a body with water resistive properties, an LED indicator, a pair of electrodes, and a microprocessor located within the body. The microprocessor may be connected to the LED indicator and the pair of electrodes and be configured to command energization to pass between the electrodes and to measure the conductivity of the water. The microprocessor may be further configured to energize the LED indicator to indicate that the measured conductivity of the water exceeds a exceeds a predetermined threshold indicative of a total dissolve solids threshold value.

Furthermore, a method of testing the concentration of total dissolve solids present in a water supply source using a disposable meter is also disclosed herein. The method may include the steps of projecting a current between a pair of electrodes being immersed in water, measuring the conductivity of the water between the electrodes, comparing the measured conductivity to a plurality of predetermined threshold values, and energizing an LED in a manner that is correlated to the highest threshold value met by the measured conductivity. Finally, a method for a water treatment services provider to provide a customer with improved recommendations of water treatment services is also disclosed herein. The method may comprise the steps of providing a water testing kit to a customer, the water testing kit including a disposable electronic total dissolved solids meter, instructing the customer to test the water supply source for total dissolved solids, receiving the results of the total dissolved solids test as reported by the customer, and providing the customer with a recommendation of water treatment services based upon an analysis of the received results.

DETAILED DISCLOSURE

Figure 1A:
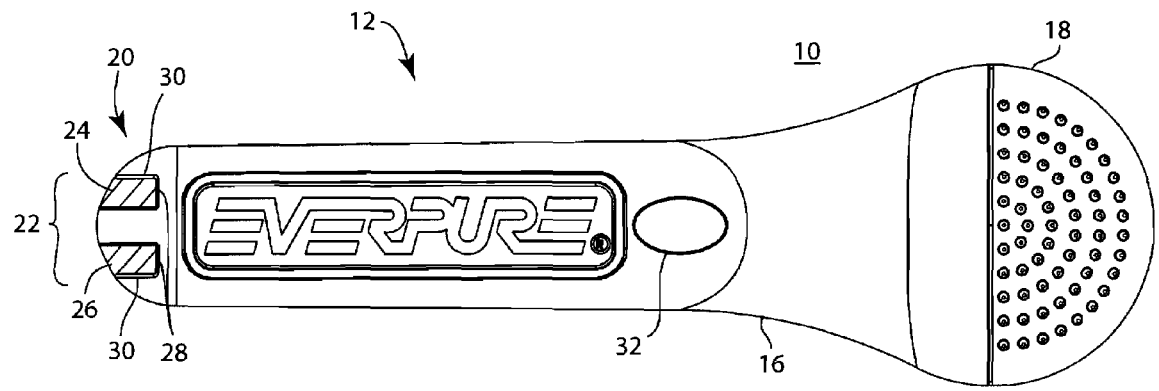
FIGS. 1a and 1b depict an embodiment of a disposable total dissolved solids meter.
Figure 1B:
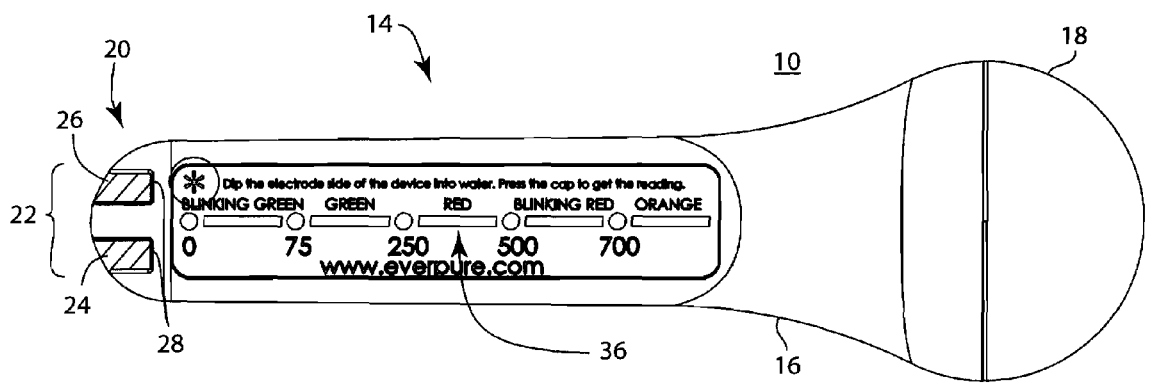

FIG. 1 depicts an embodiment of the disposable total dissolved solids (TDS) meter 10 as disclosed herein. FIG. 1a depicts the front side 12 of the disposable TDS meter 10 while FIG. 1b depicts the back side 14 of the disposable TDS meter 10. The disposable TDS meter 10 comprises a body 16. This body 16 may be constructed from a plastic or other elastomeric material, such that the construction of the body is at least water resistive. The body 16 is constructed such that it forms a hollow interior (not depicted) such that the electronics herein further detailed may be disposed at least partially within the hollow interior of the body.

An end cap 18 that may be constructed from the same or similar plastic or elastomeric material as the construction of the body 16 is attached to the body 16 at one end. In one embodiment, the end cap 18 may be attached to the body 16 by ultrasonic welding. The end cap 18 may be elastically deformable such that a button or switch (not depicted) at least partially disposed within the interior of the end cap 18 may be manipulated by a user applying pressure to the outside of the end cap 18.

The body 16 may extend elongatedly away from the end cap 18 to terminate in a tip 20. An electrode pair 22 that includes a first electrode 24 and a second electrode 26 is disposed at the tip 20 of the body 16. The first electrode 24 and the second electrode 26 are exposed to the outside by recesses 28 formed in the body 16. A seal 30 may exist respectively between the recesses 28 and the first electrode 24 and second electrode 26 respectively. The seal 30 may be at least water resistant and able to resist water of at least a minimum pressure.

Additionally, a second recess 32 exists in the body 16 such that a light admitting diode (LED) that is at least partially disposed within the body 16 is at least partially visible from outside of the body 16.

Referring now to the back side 14 of the TDS meter 10 a scale 36 is depicted on the body 16. This scale 36 provides the information necessary for a user user of the TDS meter 10 to interpret the measured total dissolve solids level by the TDS meter 10 and as indicated by the LED 34. The user may reference the indication provided by the LED 34 with the coded scale 36 to determine the parts per million (ppm) of total dissolve solids in the water source that has been tested. However, it is understood that in alternative embodiments of the TDS meter, the scale 36 is not necessary as the interpretation information may be provided elsewhere, such as with product information disseminated to the user, such as in a user's manual. Alternatively, the TDS meter may not include a scale 36 as in embodiments herein disclosed, all that is required of the user is to report the indication displayed by the LED 34.

Figure 2:
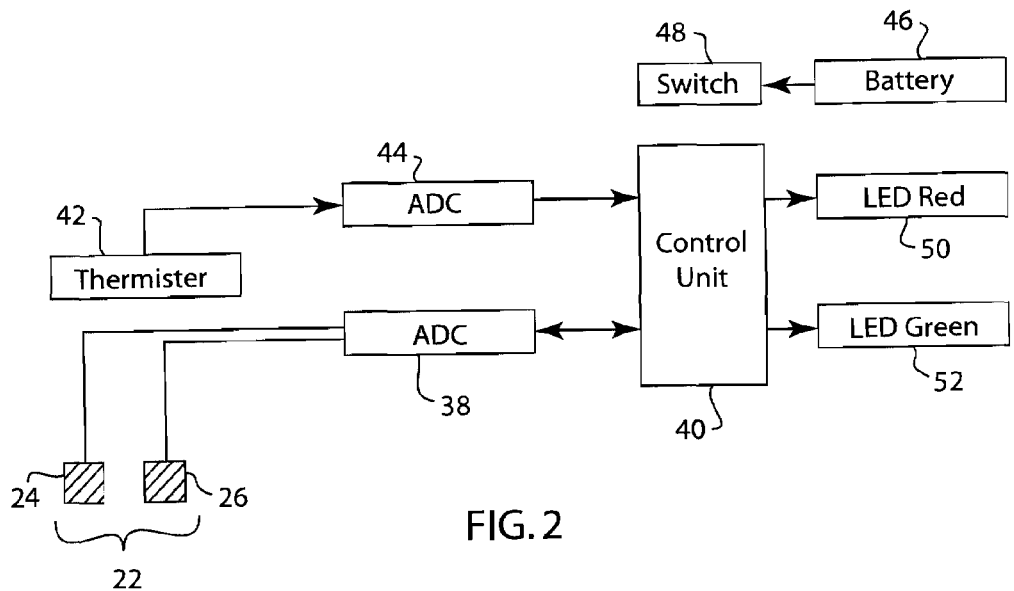
FIG. 2 is a block diagram of an embodiment of the disposable total dissolved solids meter.

FIG. 2 depicts a block diagram of an embodiment of the electrical components that may be implemented to provide functionality to the TDS meter 10. The block diagram depicts the electrode pair 22 that includes the first electrode 24 and the second electrode 26, as depicted in FIGS. 1a and 1b. The first electrode 24 and the second electrode 26 are electrically coupled to a first analog to digital converter (ADC) 38. The first ADC 38 measures the analog voltage drop between the first electrode 24 and the second electrode 26 and converts this difference to a digital value. The digital value is then sent to the control unit 40. The block diagram further depicts a thermister 42. A second ADC 44 measures the voltage across the thermister 42 and digitizes this voltage such that it may be sent to the control unit 40.

The control unit 40 may be powered by a battery 46 that is electrically coupled to the control unit 40 by a switch 48. In an embodiment, the switch 48 may be a dome switch such as the switch number XB-TL available from New Lang Technology. Alternatively, the switch 48 may be another type of suitable switch such as a push button or lever type switch as would be recognized by one skilled in the art.

Upon activation of the switch 48 the battery 46 powers the control unit 40. The digital values of the thermister voltage are provided to the control unit control unit from the second ADC 44 and the differential voltage from between the electrode pair 22 from the first ADC 38 is provided to the control unit 40. The control unit 40 uses the digitized thermister voltage to reference a look up table (not depicted) to determine the proper threshold voltage values for interpreting the electrode pair differential voltage with compensation for the measured ambient temperature.

The look up table may be stored on a separate memory component (not depicted) or may alternatively be incorporated into the hardware, software, or firmware of the control unit 40. The threshold voltages stored in the look up table may be a standardized table of threshold voltages as may be determined in a lab and stored in the look up table as part of the programming of the control unit 40. Once the control unit 40 has received the electrode pair differential voltage value from the first ADC 38, the control unit 40 provides a signal to the first ADC 38 to reverse the polarity of the electrode pair 22. Thus energization flows from the second electrode 26 to the first electrode 24. This reversal of the polarity between the electrode pair 22 helps to reduce any scaling or deposit buildup that may occur in connection with the electrode pair while the water conductivity is being tested.

Meanwhile, the control unit 40 compares the received electrode pair differential voltage to the temperature compensated threshold voltages from the look up table. Each of the threshold voltages of the look up table is associated with a specific LED control such that once the controller 40 determines the highest threshold value from the look up table that the electrode pair differential voltage meets, the control unit 40 controls a first indicator, such as a first LED 50 with respect to the programmed LED control.

As depicted in FIG. 2, the first LED 50 may be a red LED. The control unit 40 may use the single first LED 50 to denote the achievement of one of two threshold values by having one threshold value be associated with the solid energization of the first LED 50, the other threshold value being associated with the pulsating energization of the first LED 50. Alternatively the control unit 40 may be electrically coupled to a second LED 52. By the selective energization of either the first LED 50 or the second LED 52 the control unit 40 may display the achievement of up to four different threshold values of measured TDS level. It is further understood that the control unit 40 may be connected to any number of a plurality of LEDs for the indication of measured TDS level.

The lookup table is programmed with the standard threshold voltage values representative of specific levels of water conductivity that are associated with critical levels of water total dissolved solids. These values are repeated in the look up table for an operation range of temperature values such that the temperature compensation as described above may be implemented by the set of threshold values from the look up table.

In one embodiment, the threshold voltage values may be associated with the TDS levels as indicated in the table below.

| TDS Concentration | Interpretation |
|---|---|
| 0.75 ppm | Reverse osmosis treatment is functioning properly. |
| 76-150 ppm | Water is acceptable for all food service applications. |
| 151-250 ppm | Water is acceptable for all food service applications except steam<br>Ideal for coffee, espresso, and ice. |
| 251-300 ppm | Water is acceptable for all applications except steam and iced tea. |
| 301-400 ppm | Water is acceptable for drinking water and fountain beverages only<br>Low filtering capacity needed. |
| 401-500 ppm | Water is acceptable for drinking water and fountain beverages only<br>High filtering capacity needed. |
| 501-600 ppm | Reverse osmosis required for all applications. Low filtering capacity needed. |
| 601-750 ppm | Reverse osmosis required for all applications. Medium filtering capacity needed. |
| 751-900 ppm | Reverse osmosis required for all applications. High filtering capacity needed. |

Therefore, by the control unit 40 controlling the energization of at least a first LED 50, the user is able to receive an indication of the total dissolved solids concentration of the water being tested.

With reference to the above table, it may be seen that various gradations of measured TDS concentration may be determined and an indication of such display to the user. The number of specific gradations and resulting interpretations may vary from embodiment to embodiment of the TDS meter as disclosed herein. The number of interpretations provided may be a function of the distinct indications that may be created through the use of one or more indicators such as LEDs. Additional TDS concentration levels may be indicated by the energization of one or more of the indicator at a time, or the pulsating energization of one or more of the indicators.

It may also be noticed that some TDS concentrations yield the same food service application interpretation; however, the TDS concentration level yields a different indication of needed filtering capacity. This is due to the fact that TDS level in a water supply effects the volume of portable water output that may be achieved from a reverse osmosis filter system. Increased TDS levels result in fewer gallons per hour of portable water being produced by a reverse osmosis system. Therefore, in order to maintain desired levels of portable water output from the water purification system, water supplies with higher TDS levels would require reverse osmosis systems of a higher water capacity.

Figure 3:
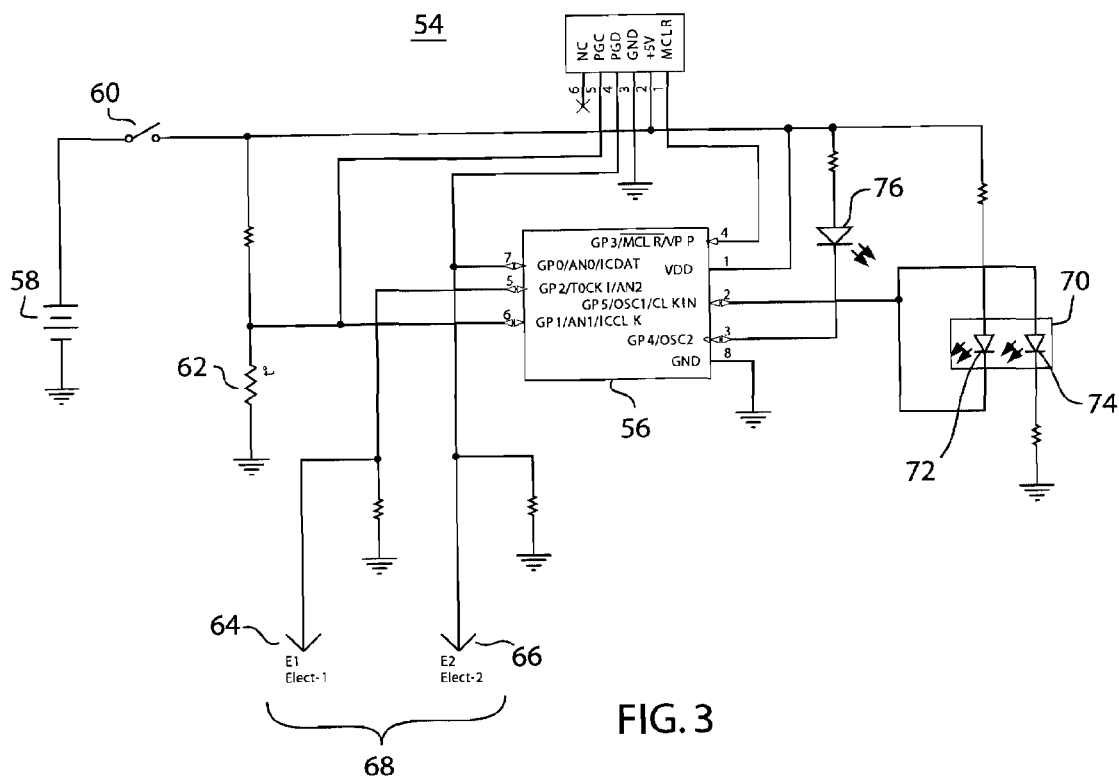
FIG. 3 is a schematic diagram of an alternative embodiment of the disposable total dissolved solids meter.

FIG. 3 depicts a schematic diagram of an embodiment of an electrical circuit 54 that may be disposed within the body 16 of the TDS meter 10, and provides the functionality of the TDS meter 10. The circuit 54 comprises a controller 56, which may be a microcontroller such as the PIC12F510 microcontroller available from Microchip. Alternatively, the controller 56 may include any suitable microcontroller, microprocessor, or combination of discrete circuitry capable of performing the functions of the controller 56 as described herein. The controller 56 is powered by a battery cell 58 which is electrically coupled to the controller 56 through a switch 60. The controller 56 receives voltage inputs from a thermister 62 and a first electrode 64 and a second electrode 66 that form an electrode pair 68.

As explained previously, the controller 56 may comprise or be operatively coupled to a look up table (not depicted) that is populated with previously determined threshold values for the differential voltage between the first electrode 64 and the second electrode 66. The predetermined threshold values are correlated to predetermined levels of water conductivity. In one embodiment the predetermined conductivity threshold values may be determined using standard salt solutions in a lab. In a still further embodiment, the conductivity threshold values may be taken from a table of predetermined, temperature compensated conductivity voltages. The controller 56 receives an indication of the ambient temperature form the voltage across the thermister 62 and uses the measured temperature to select from the look up table the proper temperature compensated threshold voltages.

The controller 56 then compares the differential voltage across the electrode pair 68 to the obtained temperature compensated threshold voltages. Each of the threshold voltages is further associated with an energization control for energizing an LED 70.

In the embodiment depicted in FIG. 3 the LED 70 is a bi-color LED that includes a green color element 72 and a red color element 74. The energization controls may selectively energize either the green color element 72 or the red color element 74. Alternatively, the energization controls may energize both the green color element 72 and the red color element 74 to produce an energization of the LED 70 that appears orange to the observing user. These three color combinations combined with the ability of the controller 56 to produce a pulsating energization of the LED 70, results in a total of 6 possible threshold values that may be indicated by the single indicated, such as an LED 70.

Once the differential voltage across the electrode pair 68 has been determined by the controller 56, the determined voltage is compared to the temperature compensated threshold voltages. The energization control that is associated with the highest threshold voltage that is met by the measured differential voltage is used to control the energization of the green color element 72 and the red color element 74 of the LED 70. Thus, the water TDS in is indicated to the user.

In an alternative embodiment, the circuit 54 may further include a second indicator, such as a second LED 76. The second LED 76 may be connected to the battery cell 58 via the switch 60 and disposed between the switch 60 and the controller 56. The second LED 76 is then energized upon the closing of the switch 60 and indicates that the circuit 54 is on and being powered. In an embodiment the second LED 76 may be of a color, such as blue, that is different that and distinguishable from, the LED 70.

In a still further alternative embodiment, the circuit 54 may further include one or more additional indicators, such as LEDs. These additional indicators may be used in conjunction with the first indicator and/or the second indicator to expand the number of TDS levels that may be indicated to the user. The one or more additional indicators may be used in conjunction with the bi-color LED 70 such that three different LED colors may be energized in different combinations to indicate various measured levels of TDS in a water supply. In some of these embodiments, the at least one additional indicator may be a blue color LED, such that the energize color is distinguishable from the energized output of the bi-color LED 70.

Figure 4:
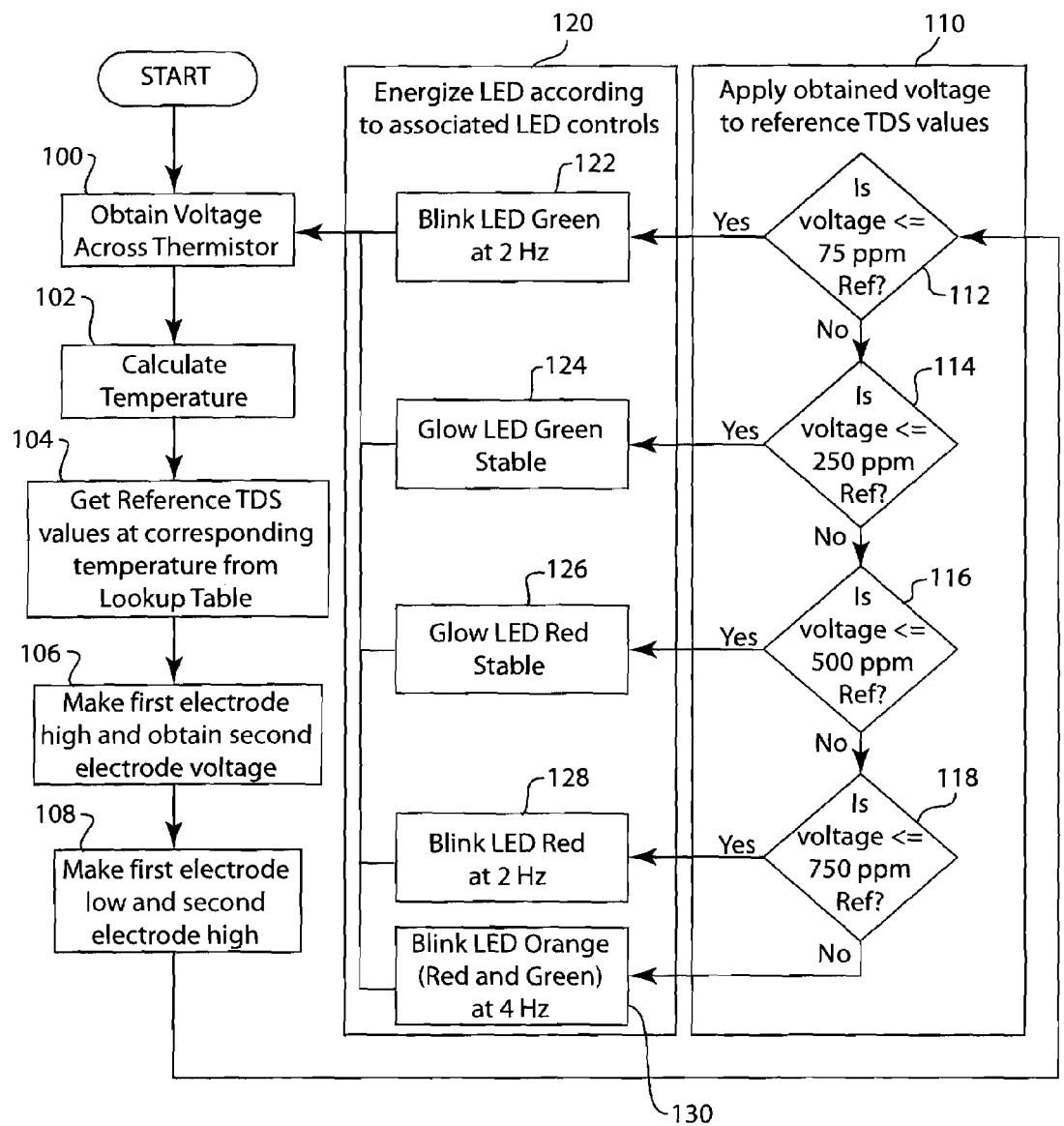
FIG. 4 is a flow chart depicting an embodiment of a method for measuring total dissolved solids.

FIG. 4 is a flow chart that depicts the steps in an embodiment of a method for determining the total dissolved solids in a water source and indicating the results to a user. The steps as depicted in the flow chart of FIG. 4 may be performed by either of the systems as described above with respect to FIGS. 2 and 3, but may also be implemented in many other systems as would be apparent to one skilled in the art in view of this disclosure. First the voltage across a thermister is obtained at step 100. Next, the voltage obtained from the thermister is used to calculate the ambient temperature at step 102. The temperature may be calculated by use of a reference table that converts the measured voltage or thermister resistance to a scaled temperature output. The voltage may be the analog voltage that is obtained off of the thermister, or the voltage may have been subject to digital processing such as analog to digital conversion and/or filtering prior to the calculation of the temperature at step 102. Next, temperature at step 102. Next, at step 104, the calculated temperature is used to select the desired reference TDS threshold values from a look up table.

When the electrode pair has been immersed in the water that is to be tested at step 106, the first electrode is set to a predetermined high energization and the voltage at the second electrode is obtained. Thus, in step 106 the electrical current flows from the first electrode to the second electrode as permitted by the conductivity of the water being tested. Thus, the differential voltage between the first electrode and the second electrode is correlated to the conductivity, and thus the TDS, of the water supply being tested. The voltage obtained from the second electrode may be used in its analog state, or may undergo signal processing such as A to D conversion or frequency modulation.

Next, the polarity of the first and second electrodes is switched at step 108 such that the first electrode has a low energization and the second electrode has a high energization. The reversal of the polarities of the first and second electrodes serve to reduce any scaling or deposit build up that may have accumulated on the electrodes during the testing of the conductivity in step 106. The performance of step 108 may improve performance of the method in future repetitions on the same device.

Next, at step 110, the voltage obtained in step 106 is applied to the reference TDS values obtained in step 104. Step 110 is exemplarily described with the implementation of sub-steps 112-118 in which the obtained voltage is applied to each of the reference TDS values. In the application of sub-steps 112-118, the obtained voltage is compared to each of the reference TDS values in turn to determine in which TDS value range the tested water sample falls. It is understood that a sufficient number of substeps may be applied in step 110 to evaluate any voltage obtained in step 106 with the desired TDS measurement specificity. Such substeps may include those associated with any or all of the TDS threshold values identified in the table above.

When the corresponding TDS reference value has been determined in step 110, these results are applied in step 120 wherein the LED is energized according to the associated LED controls which are depicted as alternative substeps 122-130. Each TDS result obtained in step 110 is associated with an LED control (122-130) in step 120. The LED is energized according to these LED controls to indicate to a user the measured TDS range of the tested water supply sample. It should be noted that the indication energizations are merely exemplary of the indication energizations that may be made. Such energizations may be dictated by the number of LED's to be energized and/or the number of TDS threshold values to indicate.

After step 120 the method returns to step 100 wherein the method is repeated to obtain a refreshed measurement of TDS. In one embodiment, a TDS meter may perform the steps of the method as depicted in FIG. 4 in a continuous loop as long as a power or activation button is depressed. Alternatively, the method may only be performed once per each time that the TDS meter is activated. In a still further embodiment, step 108 may be performed in parallel with steps 110 and 120, or alternatively, step 108 may be performed after 120, but before the method returns to step 100. It is understood that step 108 may be performed at any time prior to the next time that step 106 is performed.

Figure 5:
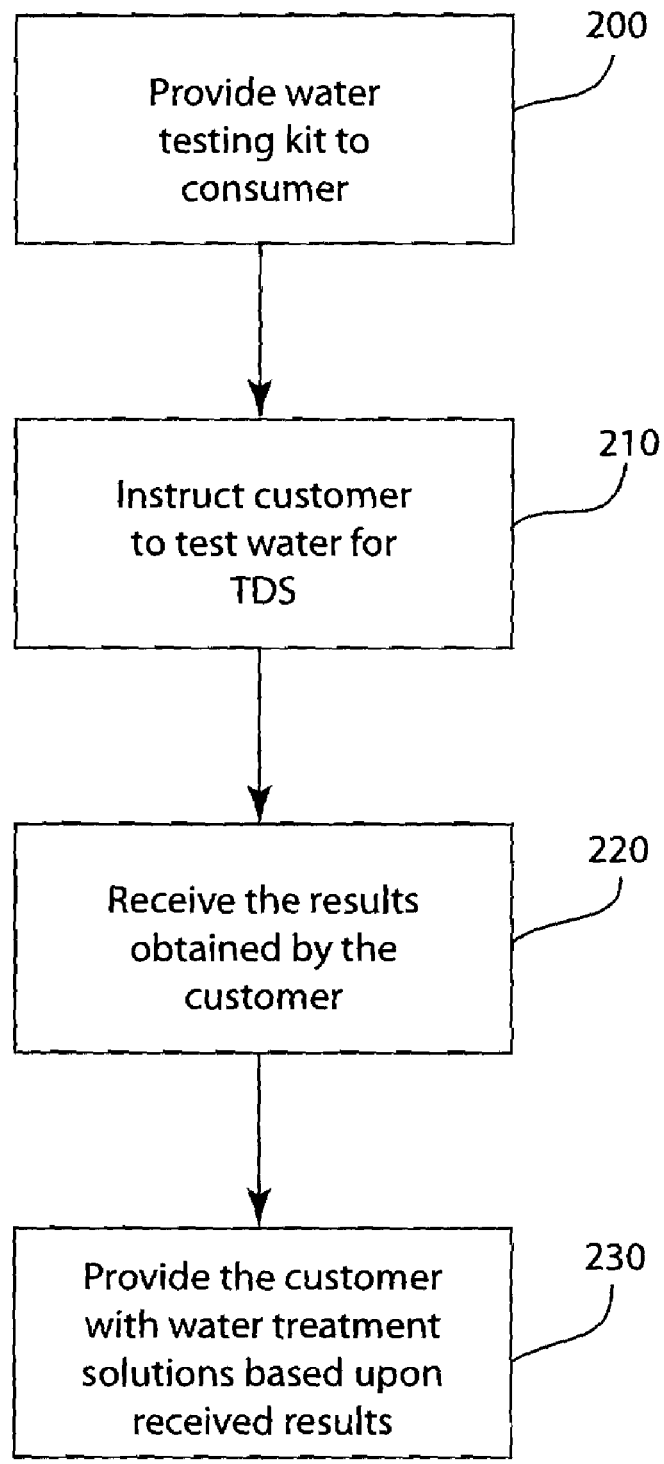
FIG. 5 is a flow chart depicting a method of providing a customer with improved recommendation of water treatment services.

FIG. 5 depicts a flow chart depicting the steps of an embodiment of a method for a water treatment services provider to provide a customer with improved recommendations of water treatment products or services. First, a water testing kit is provided to a customer at step 200. In this step a "customer" may include an active customer or a potential customer of the water treatment services provider. The water testing kit may be provided to the customer by mail or provided to the customer after a consultation or visit to a retail store. It is understood that the water testing kit may be provided in any number of alternative fashions resulting from the business needs and model of the water treatment services provider. The water testing kit includes at least a disposable electronic total dissolved solids meter, but may also include pH test strips, free chlorine test strips total chlorine test strips, water hardness test strips, water hardness test strips, alkalinity test strips, chloride test strips, and iron-test reagent powder; however, this list is in no way meant to be limiting on the scope of additional water testing equipment that may be included in the water testing kit that is provided to the customer in step 200. Next, the customer is instructed at 210 to test the water for total dissolved solids using the TDS meter in the kit. The step of instructing may include the verbal provision of instructions to the customer, or the inclusion of written instructions as a part of the water testing kit provided to the customer. The customer may further be instructed through the use of online resources made available to the customer upon receipt of the water testing kit. Additionally, the step of instructing the customer at step 210 may further include instructing the customer to test the water supply source for water pH, total chlorine free chlorine, total iron, total alkalinity, water hardness, and/or total chloride. It is further understood that this preceding list of tests to be performed by the customer is merely exemplary and is not intended to be limiting on the scope of tests that the customer may be instructed to perform.

Next, the water treatment services provider receives the results obtained by the customer at step 220. These results may be received by the water treatment services provider in any of a variety of ways as would be understood by one skilled in the art, such as the return of results by mail, the reporting of results in person, the reporting of results by phone, or the reporting of results via the internet. Finally, at step 230, the customer is provided with suggested water treatment solutions based upon the received results. The water treatment services provider in this step utilizes the results obtained by the customer in step 220 to put together a package of recommended water treatment products and/or services that fit the customer's water treatment needs, based upon the customer's industry and the impurities detected in the water as identified by the provision of the previous steps.

Therefore, the method as presented in FIG. 5 has the benefit of allowing the customer, who may have little or no knowledge regarding water testing or treatment, to provide a detailed analysis as to the customer's water treatment needs and and challenges. The water treatment service provider benefits in that a water treatment technician is not required to travel in person to customers at remote locations, but rather the customers can provide the required information to the water treatment services provider at a central location.

Thus, the water treatment services provider is able to more efficiently use resources to focus on the development and implementation of water treatment solutions.

The method as disclosed with respect to FIG. 5 is advantageous over current methods of water supply testing and analysis in that current electronic TDS meters are prohibitively expensive to provide to a customer or potential customer as part of a basic water testing kit. The current alternative to the provision of an electronic TDS monitor is to provide the customer with paper TDS test strips. However, the paper test strips have limited reliability in the results obtained, and consumers have a difficulty in properly using the test strips and accurately reading the result as the color change of the test strip must be compared to a provided color change scale. Therefore, the method presently disclosed provides a cost effective solution wherein customers are provided with the ease and accuracy of an electronic TDS meter, but the TDS meter is designed such that it is not cost-prohibitive to provide in a widely disseminated water testing kit.

The disposable hand held electronic TDS meter as disclosed herein is advantageous as it may be constructed at a low cost and yet provide the aforementioned benefits of accuracy and ease of use. Embodiments of the disposable TDS meter as disclosed herein may achieve its cost effectiveness due to some or all of the following factors. Embodiments of the disposable TDS meter may be of a water resistant construction rather than a waterproof construction that is more expensive to obtain. Water resistant construction is suitable for an embodiment of a disposable TDS meter as the meter is not intended to be repeatedly operated and thus the likelihood of water damage over a limited number of uses is reduced. Along these same lines, embodiments of the disposable TDS meter may include a power source such as a such as a battery that is limited in its power to only allow a small number of tests to be performed. Additionally, as embodiments of the disposable TDS meter may be only intended for a low number of uses embodiments may be designed without a replaceable power source.

Alternative features of embodiments of disposable TDS meters that may help to make the embodiments cost effective include the use of look up tables that are predefined and stored in or in connection with the controller. The advantage of the use of predefined look up tables is that no calibration is needed and the look up tables reduce the amount of data processing that must be performed by the controller. Additionally, embodiments of the disposable TDS meter report the measured TDS as a range as indicated by the energization of an LED. By reporting the measured TDS as a range, less data processing is required by the controller, thus reducing controller and energy supply costs. Additionally, an use of an LED indicator offers the further advantage of being a more economical solution as compared to existing TDS meters that display the measured TDS values on an LCD screen.

Therefore, as disclosed herein, a disposable hand held electronic total dissolved solids meter is an advantageous development in the field of water testing and water treatment service industries. The development of a disposable TDS meter thus enables a water treatment service provider the ability to cost effectively implement embodiments of the method of providing improved recommendations of water treatment services as disclosed herein.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

Various alternatives and embodiments are contemplated as being with in the scope of the following claims, particularly pointing out and distinctly claiming the subject matter regarded as the invention.

What is claimed is:

1. A disposable meter for use by a technician or a consumer on location for testing the level of total dissolved solids in a water source, the meter comprising:
    a body with at least water resistive properties, formed with an open interior;
    a first indicator;
    a second indicator;
    a pair of electrodes comprising a first electrode and a second electrode wherein when the pair of electrodes are immersed in water energization may complete a circuit by passing between the first electrode and the second electrode; and
    a circuitry disposed within the body, the circuitry connected to the first indicator and the pair of electrodes, the circuitry being configured to:
        commence energization to pass from the first electrode to the second electrode;
        measure the conductivity of the water between the pair of electrodes;
        energize the first indicator if the measured conductivity value exceeds a first predetermined threshold value, the first predetermined threshold value is indicative of a first level of measured total dissolved solids; and
        energize the second indicator if the measured conductivity value exceeds a second predetermined threshold value, the second predetermined threshold value is indicative of a second level of measured total dissolved solids;
    wherein the first indicator is a first LED and the second indicator is a second LED, and the circuitry is further configured to control the first LED or the second LED to be pulsingly energized, the pulsing energization of the first LED being indicative of a third threshold level of measured total dissolved solids, and the pulsing energization of the second LED being indicative of a fourth threshold level of measured total dissolved solids.

2. The disposable meter of claim 1 wherein the circuitry is a controller and further comprising a look up table with a plurality of predetermined threshold values, the look up table being stored in conjunction with the controller, such that the controller compares the measured conductivity value with the plurality of predetermined threshold values.

3. The disposable meter of claim 2 further comprising a temperature compensation circuit and the look up table comprising a plurality of threshold values based on measured ambient temperature, wherein the temperature compensation circuit measures the ambient temperature and the controller selects the predetermined threshold values from the look up table based on the measured ambient temperature.

4. The disposable meter of claim 1 further comprising a switch electronically connected to the circuitry, the switch being disposed within an end cap, wherein upon the manipulation of the switch, energization is provided from the first electrode to the second electrode and the meter measures the conductivity between the pair of electrodes.

5. The disposable meter of claim 4 wherein, the circuitry is further configured to provide energization from the second electrode to the first electrode to clean the electrodes of any deposit buildup created while measuring the conductivity.

6. A disposable meter for use by a technician or a consumer on location for testing the level of total dissolved solids in a water source, the meter comprising:
   a body with at least water resistive properties, formed with an open interior;
   a bi-color LED comprising a first color element of a first color and a second color element of a second color, wherein energization of the first color element is indicative of a first threshold value of measured total dissolved solids and energization of the second color element is indicative of a second threshold value of measured total dissolved solids;
   a pair of electrodes comprising a first electrode and a second electrode wherein when the pair of electrodes are immersed in water, energization may complete a circuit by passing between the first electrode and the second electrode; and
   a circuitry disposed within the body, the circuitry connected to the first color element, the second color element, the first electrode, and the second electrode, the circuitry being configured to commence energization to pass from the first electrode to the second electrode, measure the conductivity of the water between the first electrode and the second electrode, energize the first color element if the measured conductivity exceeds a first predetermined threshold value and energize the second color element if the measured conductivity exceeds a second predetermined threshold value;
   wherein the first predetermined threshold value is indicative of the first threshold value of measured total dissolved solids, and the second predetermined threshold value is indicative of the second threshold value of measured total dissolved solids;
   wherein the circuitry is further configured to provide pulsating energization to at least one of the first color element and the second color element such that the pulsating energization of at least one color element is indicative of a third threshold value of measured total dissolved solids.

7. A method of testing the concentration of total dissolved solids present in a water supply source using a disposable meter, the method comprising:
   providing a disposable electronic total dissolved solids meter with an at least water resistant body with an open interior, a first electrode and a second electrode extending from the body, a first indicator, a second indicator, and a water resistive seal between the first and second electrodes and the open interior,
   projecting a current between the first electrode and the second electrode, the first and second electrodes being immersed in the water to be tested;
   measuring the conductivity of the water between the first electrode and the second electrode;
   comparing the measured conductivity to a plurality of threshold values; and
   energizing the first indicator if the measured conductivity exceeds a first predetermined threshold value of the plurality of threshold values;
   energizing the second indicator if the measured conductivity exceeds a second predetermined threshold value of the plurality of threshold values; and
   energizing at least one of the first indicator and the second indicator with pulsating energization if the measured conductivity exceeds a third predetermined threshold value of the plurality of threshold values;
   wherein the first predetermined threshold value is indicative of a first threshold value of measured total dissolved solids, the second predetermined threshold value is indicative of a second threshold value of measured total dissolved solids, and the third predetermined threshold value is indicative of a third threshold value of measured total dissolved solids.

8. The method of claim 7, further comprising providing the disposable electronic total dissolved solids meter to a potential customer to perform the method steps.

9. The method of claim 8, further comprising:
   interpreting the energization of the indicator as a value of total dissolved solids; and
   providing the customer with a recommendation of a water treatment solution.

10. A disposable meter for use by a technician or a consumer on location for testing the level of total dissolved solids in a water source, the meter comprising:
    a body with at least water resistive properties, formed with an open interior;
    a first indicator;
    a second indicator;
    a pair of electrodes comprising a first electrode and a second electrode wherein when the pair of electrodes are immersed in water, energization passes between the first electrode and the second electrode; and
    a circuitry disposed within the body, the circuitry connected to the first indicator, the second indicator, and the pair of electrodes, the circuitry being configured to commence energization to pass from the first electrode to the second electrode, measure the conductivity of the water between the pair of electrodes, and energize the first indicator if the measured conductivity value exceeds a first predetermined threshold value, energize the second indicator if the measured conductivity value exceeds a second predetermined threshold value, and energize at least one of the first indicator and the second indicator with pulsating energization if the measured conductivity value exceeds a third predetermined threshold value;
    wherein the first predetermined threshold value is indicative of a first threshold value of measured total dissolved solids, the second predetermined threshold value is indicative of a second threshold value of measured total dissolved solids, and the third predetermined threshold value is indicative of a third threshold value of measured total dissolved solids.

11. The disposable meter of claim 10, further comprising a water resistive seal between the pair of electrodes and the body, the water resistive seal impeding water flow into the open interior of the body.

12. A method of testing the concentration of total dissolved solids present in a water supply source, the method comprising:
  providing a potential customer with a disposable meter comprising:
    a body with at least water resistive properties, formed with an open interior;
    a first indicator;
    a second indicator;
    a pair of electrodes comprising a first electrode and a second electrode wherein when the pair of electrodes are immersed in water, energization passes between the first electrode and the second electrode; and
    a circuitry disposed within the body, the circuitry connected to the first indicator, the second indicator, and the pair of electrodes, the circuitry being configured to commence energization to pass from the first electrode to the second electrode, measure the conductivity of the water between the pair of electrodes, and energize the first indicator if the measured conductivity value exceeds a first predetermined threshold value, energize the second indicator if the measured conductivity value exceeds a second predetermined threshold value, and energize at least one of the first indicator and the second indicator with pulsating energization if the measured conductivity value exceeds a third predetermined threshold value;
    wherein the first predetermined threshold value is indicative of a first threshold value of measured total dissolved solids, the second predetermined threshold value is indicative of a second threshold value of measured total dissolved solids, and the third predetermined threshold value is indicative of a third threshold value of measured total dissolved solids.
  instructing the customer to test the water supply source for at least total dissolved solids;
  receiving a total dissolved solids measurement obtained by the customer; and
  providing the customer with a recommendation of water treatment services based upon an analysis of the received results.

* * * * *